United States Patent [19]

Olson et al.

[11] 4,402,222

[45] Sep. 6, 1983

[54] BOLT LOAD DETERMINING APPARATUS

[75] Inventors: Gene E. Olson; Donald D. Grover; Christopher B. Stout; Thomas P. Becker; Glenn A. Kaufman, all of Kenosha; Norbert J. Kot, Milwaukee, all of Wis.

[73] Assignee: Snap-on Tools Corporation, Kenosha, Wis.

[21] Appl. No.: 342,901

[22] Filed: Jan. 26, 1982

[51] Int. Cl.³ .................... G01H 13/00; G01N 29/00
[52] U.S. Cl. ........................................ 73/579; 73/761
[58] Field of Search .................... 73/579, 580, 761

[56] References Cited
U.S. PATENT DOCUMENTS 4,014,208  3/1977  Moore et al. ........................ 73/629
4,117,731  10/1978  Heyman ............................... 73/579
4,363,242  12/1982  Heyman ............................... 73/629

Primary Examiner—Howard A. Birmiel
Attorney, Agent, or Firm—Dithmar, Stotland, Stratman & Levy

[57] ABSTRACT

A first signal at a first frequency which is a selected harmonic of the resonant frequency of a bolt in a first loaded condition is determined. Then there is determined a second signal at a second frequency being the same harmonic of the resonant frequency of the bolt in a second loaded condition. Both frequencies are multiplied by a factor M. The up input of a counter receives one of the signals for a predetermined duration, and the down input receives the other signal for the same duration. The number of pulses remaining in the counter is representative of the difference in load between the first and second loaded conditions.

30 Claims, 7 Drawing Figures

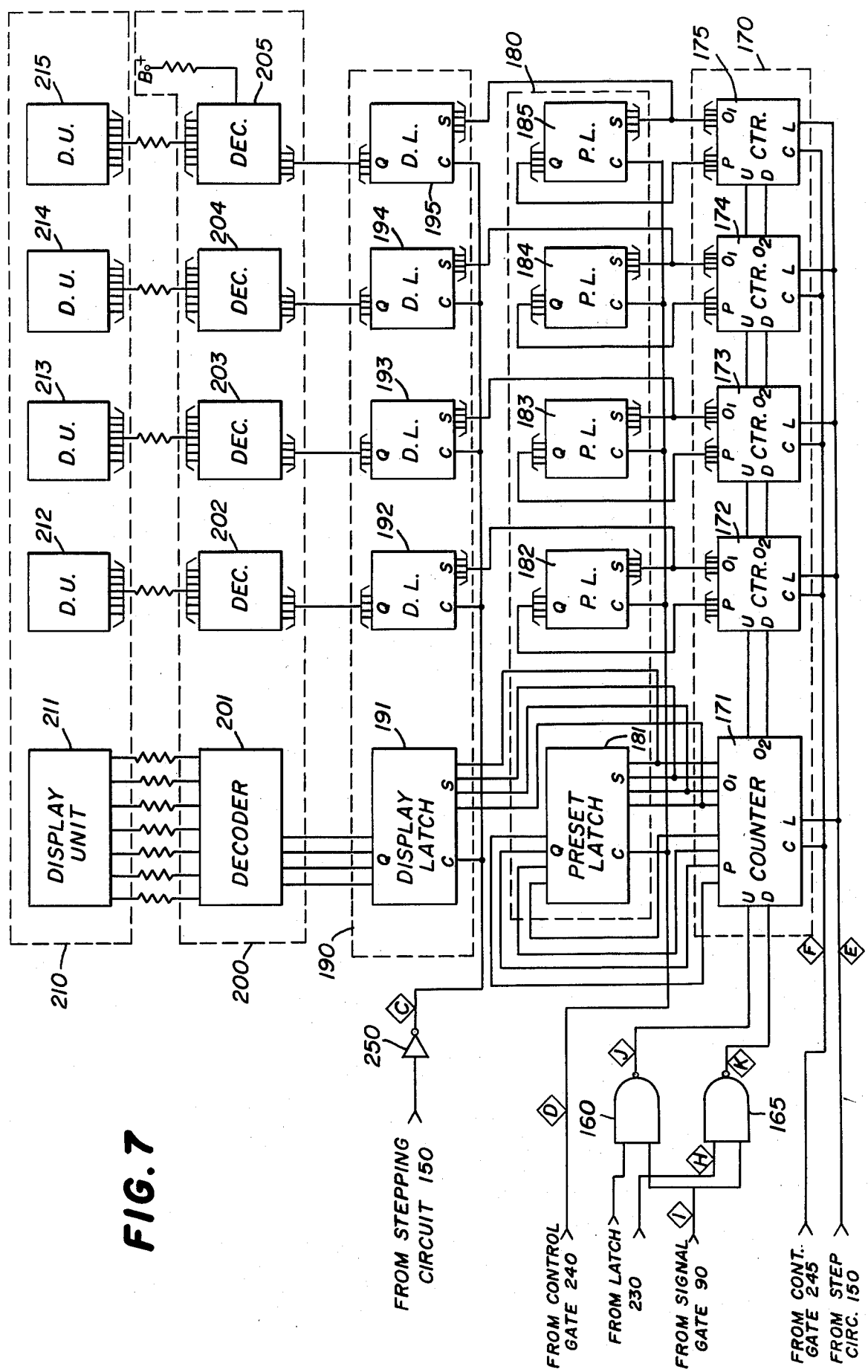

BOLT LOAD DETERMINING APPARATUS

BACKGROUND OF THE INVENTION

Tightening of threaded fasteners to the proper load is of great importance. Torque wrenches which have been widely used for many years for controlling fastener loads suffer the disadvantages of relying on torquetension relationship which varies with friction due to lubrication for example and results in questionable accuracy of load measurements.

Another type of bolt load determining apparatus involves tightening the bolt to its yield point. Most such units are large and are part of permanent installations. Tightening a bolt to its yield point may be undesirable in many situations.

Prior systems generally suffer the disadvantages of need for special fasteners components, extensive time to make the measurements, special access for clearances, and expensive power equipment.

In response to these undesirable features of available bolt load testing systems then on the marketplace Dr. Joseph Heyman devised an ultrasonic instrument described in his U.S. Pat. No. 4,117,731.

The patented system includes a transducer which is affixed to one end of the bolt under test. Signals are produced at a harmonic of the resonant frequency of the bolt. The instrument produces signals almost continuously (99.8% of the time). But, for a short part of each cycle (0.2%), the system evaluates the response of the bolt to the signal. A bolt has a bell-shaped response curve when frequency is plotted against energy. The peak in energy represents the frequency at which the bolt is resonant. The frequency is fairly low and is in the audible range. However, there are minor peaks representing resonance at harmonics of the resonant frequency. Dr. Heyman determined that if high frequencies are selected, a node for most bolts will fall within a selected range such as 4.8–5.2 mHz. A given bolt may be resonant at say 5 mHz which is, for example, the 127th node.

The patent describes adjusting the variable phase shifter 27 in the Heyman instrument until the output is maximized. The frequency of resonance is displayed on the readout 34. First, the frequency of resonance is determined for the bolt in its unloaded condition. When the bolt is thereafter tightened, the frequency of the resonant peak will shift, as described in the patent, and the new frequency of resonance will be continuously displayed on the readout 34.

Basically, the Heyman instrument causes the frequency applied to the bolt to always be such that it is at the same node. In other words, if in making the initial adjustment, the 127th node is selected, and the bolt is then stressed to cause its resonant frequency to change, the frequency applied to the bolt will not only be such as to place it in resonance, but also to place it in resonance at the same node.

The difficulty with the Heyman instrument is that the frequency of resonance of the unstressed bolt and/or the stressed bolt is not useful in and of itself. The frequency must be translated to load on the bolt.

SUMMARY OF THE INVENTION

It is therefore an important object of the present invention to utilize the Heyman instrument to obtain the load in a bolt.

Another object is to provide digital reading of the load in a bolt.

Another object is to provide an instrument which will very accurately determine the load in a bolt.

Another object is to require access to only one end of the bolt when its load is being evaluated.

Another object is to provide a versatile bolt load testing instrument which will determine the load in a variety of fastener sizes and materials.

Another object is to provide a bolt load determining instrument which does not require tightening to the bolt's yield point.

Another object is to provide an instrument which either analyzes an initially unloaded bolt which is thereafter loaded and determines the load in the bolt, or analyzes an initially loaded bolt which is thereafter unloaded and determines the initial load in the bolt, or determines the change in load between two other loaded conditions of the bolt.

In summary, there is provided bolt load determining apparatus comprising means for providing a first pulsating signal at a first frequency being a selected harmonic of the resonant frequency of the bolt in a first loaded condition thereof and for thereafter providing a second pulsating signal at a second frequency being the same harmonic of the resonant frequency of the bolt in a second loaded condition thereof, means for multiplying the first frequency by a factor M dependent on the first frequency and the geometry and composition of the bolt and thereafter multiplying the second frequency by the factor M, counter means having an up input to receive pulses to be counted up from zero and a down input to receive pulses to be counted down from the number counted at the up input, means for coupling the first pulsating signal to one of the inputs for a predetermined duration and for thereafter coupling the second pulsating signal to the other of the inputs for the predetermined duration, and means for indicating the number of pulses remaining in the counter means which number is representative of the difference in load on the bolt between the first and second loaded conditions.

In another form of the invention, there is provided a method for determining the load in a bolt, comprising the steps of providing a bolt in a first loaded condition, providing a first pulsating signal at a first frequency being a selected harmonic of the resonant frequency of the bolt in the first loaded condition, multiplying the first frequency by a factor M dependent on the first frequency and geometry and composition of the bolt, counting the number of pulses of the first pulsating signal for a predetermined duration, storing such number, changing the loading on the bolt to a second loaded condition, providing a second pulsating signal at a second frequency being the same selected harmonic of the resonant frequency of the bolt in its second loaded condition, multiplying the second frequency by the factor M, counting away from the stored number the number of pulses of the second pulsating signal for the same predetermined duration, and indicating the number of pulses remaining after counting away from the stored number.

The invention consists of certain novel features and a combination of parts hereinafter fully described, illustrated in the accompanying drawings, and particularly pointed out in the appended claims, it being understood that various changes in the details may be made without departing from the spirit, or sacrificing any of the advantages of the present invention.

BRIEF DESCRIPTION OF THE DRAWINGS

For the purpose of facilitating an understanding of the invention, there is illustrated in the accompanying drawings, a preferred embodiment thereof, from an inspection of which, when considered in connection with the following description, the invention, its construction and operation, and many of its advantages should be readily understood and appreciated.

FIGS. 3-7 are diagrams partially in logic and partially in block depicting details of the blocks of FIG. 1.

DESCRIPTION OF THE PREFERRED EMBODIMENT

When a bolt is tightened to cause it to become stressed, two phenomena take place: it becomes longer so that the path traversed by sound waves is longer and the velocity of sound decreases. It has been determined that about ⅓ of the change in frequency from an unstressed condition to a stressed condition is due to the change in length of the bolt, while about ⅔ of that change is due to the change in velocity. Stated another way:

$$\frac{\Delta F}{F_u} = K \frac{\Delta L}{L}$$

In the above formula, $F_u$ represents the frequency at a selected harmonic (e.g. 127th) of the resonant frequency of the bolt in its unloaded condition, $\Delta F$ represents the change in frequency between the unloaded condition and its loaded condition, L represents the initial length of the bolt, $\Delta L$ represents the change in length, and K represents a constant. K would be precisely 3 if the relationship were ⅓, ⅔ as mentioned above. It turns out that K is dependent upon the composition of the bolt. For certain compositions of steel, K is about 3.38.

The formula for elongation of a long rod is:

$$\Delta L = \frac{PL}{AE}$$

In the above formula, P is the load in the bolt, A is its cross sectional area, and E is Young's modulus.

Both formulas may be solved for P as follows:

$$P = \Delta F \left[ \frac{LE}{F_u K} \left( \frac{A_{t1}}{L_{t1}} + \frac{A_{t2}}{L_{t2}} + \frac{A_u}{L_u} \right) \right]$$

$A_u$ and $L_u$ are respectively the cross-sectional area and length of the unthreaded portion of the bolt; $A_{t1}$ and $L_{t1}$ are respectively the cross-sectional area and length of that part of the threaded portion of the bolt between the head and the nut; and $A_{t2}$ and $L_{t2}$ are respectively the cross-sectional area and effective length of that part of the threaded portion of the bolt within the nut. Although the head of the bolt is also under stress, it has been empirically determined that such stress has little or no effect. Also, that part of the threaded portion of the bolt protruding from the nut has no effect either. In the above definition of $L_{t2}$, "effective length" is used because the stress in such threaded portion is not constant. It has been determined empirically that the effective length $L_{t2}$ is about ½ the major diameter of the threaded portion of the bolt. In these definitions, it is assumed that a bolt is attached to a nut, but the same principles would be applicable if the bolt was attached in a tapped hole. The "effective length" in such case may be more complex.

Figure 1:
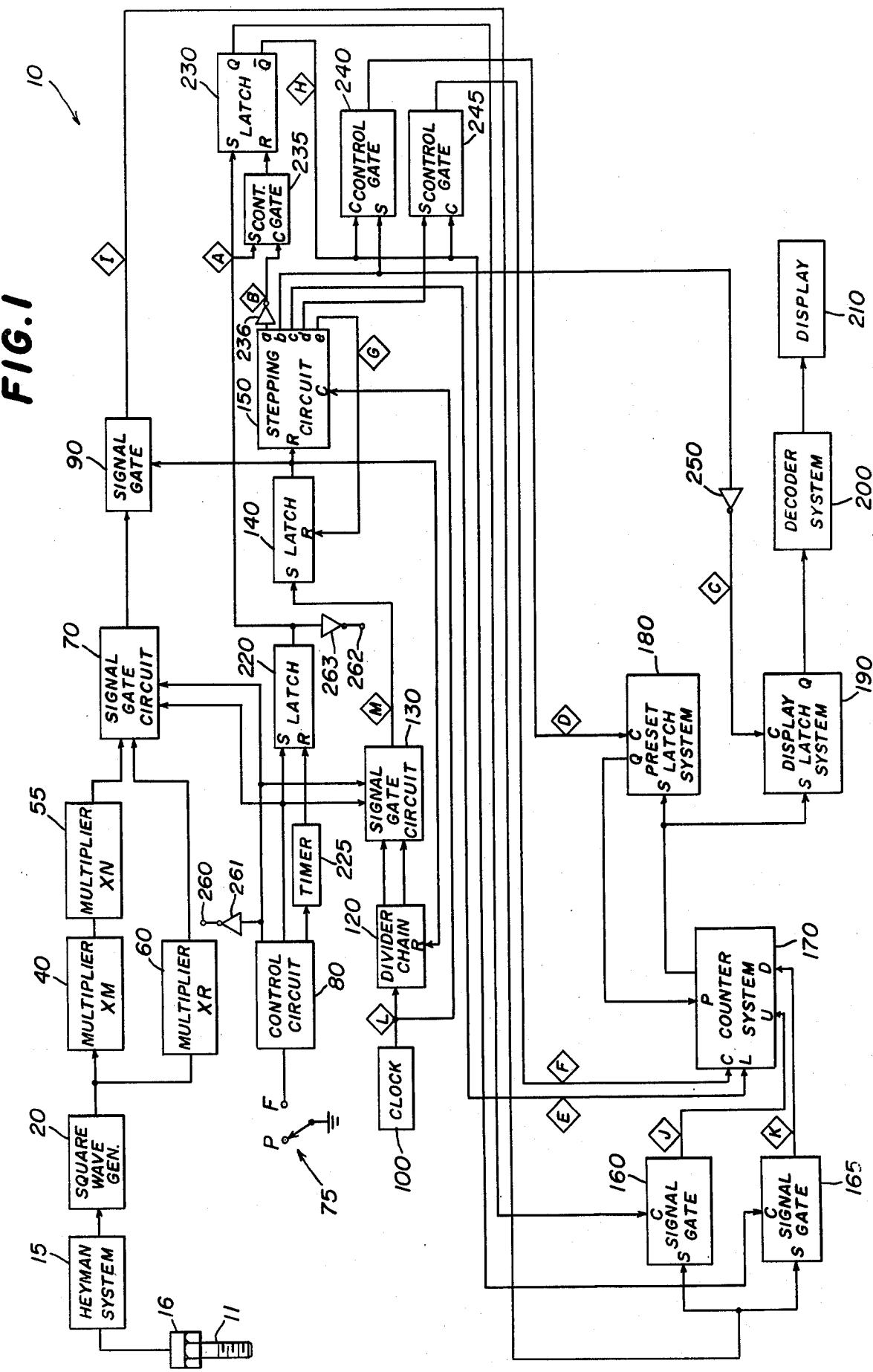
FIG. 1 is a block diagram of a bolt load determining apparatus incorporating the features of the present invention.

The bracketed material is referred to as the factor M which if multiplied by the change in frequency $\Delta F$ gives the load in the bolt. The Heyman instrument is designed to identify the frequencies when the bolt is unloaded and when it is loaded. FIG. 1 depicts an apparatus 10 including a Heyman system 15. The apparatus 10 first identifies the frequency $F_u$ of the unloaded bolt which is required to compute the factor M. Then it multiplies $\Delta F$ by M to obtain the load; i.e. $P = F_u M - F_p M$ in which P is the load and $F_u$ and $F_p$ are the frequencies when the bolt 11 is respectively unloaded and loaded. Under test is a bolt 11 having a threaded portion, an unthreaded portion and a head. The Heyman system 15 constructed basically like that shown in U.S. Pat. No. 4,117,731 entitled "Pseudo Continuous Wave Instrument" and the entirety of such patent is incorporated herein by reference. The Heyman system 15 generates a radio frequency on the order of 5 mHz which is applied to a transducer 16 that converts the electrical radio frequency signals to acoustic waves which are introduced into the bolt 11. Means are provided in the Heyman system to adjust the frequency of the RF signals to match a harmonic of the resonant frequency of the bolt 11 in a selected range of, for example 4.8 to 5.2 mHz. Although obtaining such frequency may be accomplished as described in the patent by adjusting the variable phase shifter disclosed therein, it may also be accomplished by adjusting a potentiometer in Heyman's summing amplifier 18 while monitoring the voltmeter 33 described in the patent. Maximization of the reading on the voltmeter means that a node has been found. When the bolt 11 is thereafter tightened, the Heyman system 15 automatically causes the frequency applied to the bolt to always be such that it is at the same node. The irregular sine wave produced by the Heyman system 15 is applied to a square wave generator 20 which produces a pulsating signal at the same frequency. After the factor M is calculated it is programmed into a first multiplier 40 by adjusting user accessible means therein. Thus, the multiplier 10 will develop a signal having a frequency $F_u M$ when the bolt 11 is unloaded and a frequency $F_p M$ when the bolt 11 is loaded. A second multiplier 55 multiplies the frequency by an additional, fixed factor N of say 0.5 to assist in establishing the number of digits in the number display that represents the magnitude of the load P. Further details follow.

In order to determine $F_u$, the pulsating signal from the square wave generator 20 is acted upon by a third multiplier 60 which, as will be explained, is also used to obtain the desired number of digits in the displayed number that represents the magnitude of $F_u$. The factor R contributed by the multiplier 60 could be 1, although in the preferred embodiment it is 0.1.

Actually, all three multipliers 40, 55 and 60 are continuously operative so that two multiplied pulsating signals are continuously applied to a signal gate circuit 70 which selects the one to pass.

To select the condition of the signal gate circuit 70 there is provided a manual switch 75 having its fixed contact connected to ground and having an "F" or frequency position and a "P" or load position. The switch 75 is connected to a control circuit 80 having two outputs coupled to the control inputs of the signal gate circuit 70. In the "F" position of the switch 75, the control circuit 80 develops a voltage on the control inputs of the signal gate circuit 70 to cause it to gate through the multiplied pulsing signal developed by the multiplier 60, that is, $F_uR$ when the bolt 11 is unloaded and $F_pR$ when the bolt is loaded.

There is no reason to load the bolt 11 when the switch 75 is in its "F" position and therefore as a practical matter, the signal gate circuit 70 would not normally produce a pulsating signal having the frequency $F_pR$. In the "P" position of the switch 75, the voltage developed by the control circuit 80 causes the signal gate 70 to gate through the pulsating signal from the multipliers 40 and 55, that is, a pulsating signal with a frequency $F_uMN$ when the the bolt 11 is unloaded with $F_pMN$ when the bolt is loaded.

The signal from the signal gate circuit 70 is applied to the signal input of another signal gate 90 which is operative to pass the signal applied thereto when and during the presence of a timer signal at its control input. Such timer signal has a predetermined duration and is produced in the following manner.

The apparatus 10 includes a clock 100 which generates a clock signal at a frequency of 1 mHz, for example. The signal is depicted in FIG. 2L. The frequency is reduced and the period increased by a divider chain 120 which has outputs at frequencies of 10 Hz and 5 Hz in the preferred embodiment. The clock 100 is free running, but the divider chain 120 operates only when an enabling voltage appears on its reset input R. Thus, there appears on the two outputs of the divider chain 120 two control signals both commencing with the appearance of the enabling voltage on the reset input, but having two different durations. In the example of signals with frequencies of 10 Hz and 5 Hz, the control signals will have durations of 0.1 and 0.2 second respectively.

The apparatus 10 includes another signal gate circuit 130 having its signal inputs coupled to the divider chain 120 and its control inputs coupled to the control circuit 80. The signal gate circuit 130 performs and is constructed like the signal gate circuit 70. In the "F" position of the switch 75, one control signal is utilized while in the "P" position, the other control signal is utilized. The signal gate circuit 130 has means to differentiate the control signal applied thereto so that there appears on its output a pulse occurring either one predetermined time (0.1 second, e.g.) after reset or another time (0.2 second, e.g.) after reset. The pulses appearing at the output of the signal gate circuit 130 are depicted in FIG. 2M. The first such pulse appears at time $t_1$. Reset of the divider chain 120 occurs at time $t_2$ and the pulse from the signal gate circuit 130 occurs at time $t_4$, the predetermined time interval between the two being labeled "d". In the above example, the predetermined time interval d is 0.1 second in the "F" or frequency position of the switch 75. In the "P" or load position of the switch 75, the predetermined time interval starts at time $t_6$ and may be, for example, 0.2 second.

The pulse on the output of the signal gate circuit 130 is coupled to the set input of a latch 140 causing termination of the timer signal which had been present on its output. The output of the latch 140 is coupled to a stepping circuit 150 which has five outputs "a" to "e". When the stepping circuit 150 is enabled by virtue of the termination of the timer signal on the reset input, enabling pulses successively appear on such outputs. The clock input C of the stepping circuit 150 receives clock pulses from the clock 100. The enabling pulse appearing on the last output "e" of the stepping circuit 150 is coupled back to the reset input of the latch 140 causing it to be reset and the timer signal on the output thereof to commence, thereby initiating the reset voltage on the R input of the stepping circuit 150. One enabling pulse on the output terminal "e" is shown in FIG. 2G, at time $t_2$. That pulse has negligible width because as soon as the pulse commences, the latch 140 becomes reset and the reset voltage on the stepping circuit initiates thereby terminating the enabling voltage on the "e" output.

When the latch 140 is reset at time $t_2$, the timer signal on its output commences. The timer signal commencement is fed back to the reset input of the divider chain 120 and one of the two predetermined times later, as determined by the setting of the switch 75, a pulse appears at the output of the signal gate circuit 130 to set the latch 140 and terminate the timer signal. Thus, there appears on the output of the latch 140 a timer signal commencing at $t_2$ and terminating at $t_4$, the duration of which timer signal is d.

Continuing with the example, if the predetermined duration is 0.1 second in the "F" position of the switch 75, the unloaded frequency $F_u$ is 5 mHz and the factor R is 0.1, a chain of 50,000 pulses will appear at the output of the signal gate 90. Thus, when counted in ensuing stages, five decades of display can be used to represent seven decades of frequency. In the "P" position, the multipliers 40 and 55 are in effect. If say 1.5 mHz is derived from the multiplier 40, a factor N of 0.5 and a 0.2 second predetermined time interval will cause a chain of 150,000 pulses to appear at the output of the signal gate 90. In ensuing stages when the pulses are counted and displayed, six decades of accumulated pulses are represented by five decades of display of load.

The output of the signal gate 90 is shown in FIG. 2I. Pulses appear on such output during the time interval $t_2-t_4$. The pulses from the signal gate 90 are applied to the signal inputs of signal gates 160 and 165, the outputs of which are respectively coupled to the "up" input and "down" inputs of a counter system 170. As will be explained, the signal gate 160 is operative to gate through pulses from the signal gate 90 when the switch 75 is in the "F" position, and the signal gate 165 is operative to gate through pulses from the signal gate 90 when the switch 75 is in the "P" position. The output of the counter system 170 is coupled to a preset latch system 180, the Q output of which is coupled back to the preset input P of the counter system 170. If pulses are coupled through the signal gate 160, the counter system 170 counts up from zero and the number of such pulses is coupled to the signal input S of the preset latch system 180. On the other hand, pulses coupled through the gate 165 are counted down by the counter system 170 from whatever number was at its preset input P. The preset latch system 180 has a control input C, and when a control signal is applied thereto, the number of pulses counted by the counter system 170 and applied to the signal input S is gated through to its Q output which in turn is applied to the preset input P of the counter system 170. The counter system 170 has a load input L and a clear input C. When a control signal is applied to the L input, the number at the P input is loaded in. When a control signal is applied to the C input, the counter system 170 is cleared. The output of the counter system 170 is also applied to the signal input S of a display latch system 190. When a control signal is applied to its control input C, the number which had been applied to the S input is gated through to a decoder system 200 which converts the binary information from the display latch system 190 into information necessary to drive a seven segment display 210.

Control for the gates 160, 165 and the systems 170, 180 and 190 will now be described. The second output of the control circuit 80 is coupled to the set input of a latch 220. A third output of the control circuit 80 is coupled to a timer 225, the output of which is coupled to the reset input of the latch 220. The output of the latch 220 is depicted in FIG. 2A. When the manual switch 75 is in the "F" position, the output of the latch 220 is low. When the switch 75 is moved to the "P" position, a voltage is applied to the set input of the latch 220 which has no effect on its output. At the same time that the control circuit 80 supplies a voltage to the set input, it also starts the timer 225 and a predetermined time thereafter, that is, at $t_3$ the output of the timer provides a reset voltage for the latch 220, causing it to switch conditions and its output to become high. In an actual embodiment, the predetermined time was 2 seconds. Basically, the latch 220 provides a signal that places the apparatus 10 in its frequency measuring condition not only when the switch 75 is in the "F" position but also for a predetermined time—such as 2 seconds—after the switch is placed in the "P" position. The reason for this operation will be described in further detail.

The output of the latch 220 is applied to the set input of a latch 230, the reset input of which is coupled to the output of a control gate 235 having its signal input coupled to the latch 220 and its control input coupled through an inverter 236 to the "a" output of the stepping circuit 150. The latch 230 has two outputs Q and $\overline{Q}$ which perform in tandem, one being high while the other is low and vice versa. The latch 230 has its Q output coupled to the control input of the signal gate 160 and its $\overline{Q}$ output coupled to the control inputs of control gates 240 and 245 and the signal gate 165. In the frequency position of the manual switch 75, the set input of the latch 230 is low causing the $\overline{Q}$ output of the latch 230 as depicted in FIG. 2H to be low and the Q output to be high. The control gates 240 and 245 are constructed to be operative when their control inputs are low, to gate through signals appearing on their signal inputs. The signal gate 160 is constructed to be enabled in the presence of the high control voltage to gate through signals on the signal input thereof. The signal gate 165 is constructed to be disabled by a low control voltage.

When the timer signal from the latch 140 terminates at $t_1$, the voltage on the reset input of the stepping circuit 150 is such as to cause its outputs "a" to "e" to produce enabling pulses successively thereon during the period $t_1$-$t_2$. As shown in FIG. 2B, the enabling pulse on the "a" output does not appear precisely at $t_1$. Instead, being controlled by pulses from the clock 100 (FIG. 2L), the stepping circuit does not start a cycle until the next negative transition of a clock pulse.

The enabling pulse on the "a" output which is inverted by the inverter 236 and applied to the control gate 235 cannot be gated therethrough because its control input is low. Thus, the pulse on the "a" output of the stepping circuit 150 has no effect in this particular sequence. The "b" output of the stepping circuit 150 then provides an enabling pulse for the signal input of the control gate 240, being operative, gates such pulse therethrough. The pulse from the control gate 240, which is shown in FIG. 2D, is coupled to the control input of the preset latch system 180. The enabling voltage thereon causes the number applied to the S input from the counter system 170 to be gated to its Q output which in turn is applied to the preset input P of the counter system 170. At the same time, as shown in FIG. 2C, the enable pulse applied through the inverter 250 to the control input of the display latch system 190 causes the number at the signal input S thereof to be gated through to the decoder system 200 which causes a number representing frequency to appear on the display 210.

Next, an enabling pulse appears on the "c" output of the stepping circuit 150 which is applied to the L input of the counter system 170 as shown in FIG. 2E, causing the number on its P input to be loaded into the counter system 170.

Next, the enabling pulse on the "d" output of the stepping circuit is applied to the signal input of the control gate 245, which being operative is gated through as shown by FIG. 2F, to the clear input C of the counter system 170 to clear any number previously loaded into it. Finally, an enabling pulse appears on the "e" output of the stepping circuit 150 as shown in FIG. 2G which operates as previously described to reset the latch 140 and start the predetermined time interval. The display 210 preferably has five decades of display read in mHz. The display 210 has a decimal point 260 energized by a voltage from the control circuit 80 applied through an inverter 261.

In the frequency mode, the decimal point 260 is energized, whereby there will appear on the display 210 a frequency in terms of X.XXXX mHz.

Summarizing, when the switch 75 is in the frequency mode, the bolt 11 is unloaded and there will appear at the output of the signal gate 90 a number of pulses being a fraction of the frequency $F_u$. Those pulses are gated through the signal gate 160, which is then operative, to the "up" input of the counter system 170. When the predetermined time is completed, no more pulses are coupled through the signal gates 90 and 160, and the stepping circuit 150 begins its cycle. The second output causes any number that had previously been stored in the display latch system 190 to appear on the display 210 which number continues to be displayed until the next time the stepping circuit 150 goes through a cycle. In other words, the display 210 is updated at a rate almost equal to the predetermined time interval, in the example being 0.1 second plus the sequence time of circuit 150.

The second enabling pulse also causes the number of pulses just counted by the counter system 170 to be gated to the Q output of the preset latch system 180 and into the preset input P of the counter system 170. The third pulse from the stepping circuit 150 loads the counter system with the number then at the preset input P. The fourth pulse clears the counter system 170 and the fifth pulse starts the predetermined time interval again so that a new count of the number of pulses during such interval can be made.

The operator of the apparatus 10 has thus been able to determine the frequency of a selected harmonic of the resonant frequency of the bolt 11. That frequency $F_u$ is used in calculating the factor M which is then programmed into the first multiplier 40. Then, the manual switch 75 is moved to its "P" position. Immediately the voltage on the control inputs of the signal gate circuit 70 is such as to gate therethrough a signal with the frequency $F_uMN$. Also, immediately with the operation of the switch 75, the signal gate circuit 130 receives signals at its control inputs to produce a pulse a different predetermined time after the divider chain was reset; for example, 0.2 second instead of 0.1 second. Initially, the latch 200 is unaffected by the shift of the switch 75. Assuming a 2 second timer 225, the output of the latch 200 changes conditions 2 seconds after the switch is shifted. Thus, during the first two seconds after shifting of the switch, the gates 160, 165, 235, 240, 245 and the latch 230 act as if the apparatus 10 is still in the frequency mode; i.e. they retain the same enablement or disablement as the case may be.

At the output of the signal gate 90 there will appear a number of pulses equal to $F_uMN$ times the predetermined time interval. That chain of pulses is applied through the still operative signal gate 160 to the "up" input of the counter system 170. On termination of the predetermined time interval, the stepping circuit 150 begins to cycle.

On termination of the predetermined time interval, the voltage on the reset input of the stepping circuit 150 is such as to cause its outputs "a" to "e" to produce enabling pulses successively thereon. The enabling pulse on the "a" output has no effect because the control gate 235 is still disabled. The "b" output of the stepping circuit 150 then provides an enabling pulse for the control gate 240 which, being operative, gates such pulse therethrough to the control input of the preset latch system 180. The enabling voltage thereon causes the number applied to the S input from the counter system 170 to be gated to its Q output which in turn is applied to the preset input P of the counter system 170. At the same time, the enable pulse applied through the inverter 250 to the control input of the display latch system 190 causes the number at the signal input S thereof to be gated through to the decoder system 200 which causes a number equal to $F_uMN$ times the predetermined time interval to appear on the display 210.

Next, an enabling pulse on the "c" output is applied to the L input of the counter system 170 causing the number on its P input to be loaded into the counter system 170. Next, the enabling pulse on the "d" output of the stepping circuit 150 is applied to the signal input of the control gate 245 which being operative is gated through to the clear input of the counter system 170 to clear any number previously loaded into it. Finally, an enabling pulse appears on the "e" output of the stepping circuit 150 which operates to reset the latch to start the predetermined time interval.

Using the example of a two-second timer 225 and a 0.2 second predetermined time interval, the apparatus 10 goes through about ten such cycles of counting and stepping. The fact that during these cycles a number appears on the display 210 is not significant because that is not meaningful to the opertor. What is meaningful is the fact that a number representing the frequency of a selected harmonic of the resonant frequency of the bolt 11 in its unloaded condition multiplied by the factor M is applied to the preset input of the counter system 170. Actually, the number is multiplied by the factor N which is 0.5 in the example. Because the predetermined time is 0.2 second in such example, the effect is to reduce the number applied to the preset input of the counter system 170 by a factor of 10. In other words, five decades of display will correspond to six decades of load.

Figure 2:
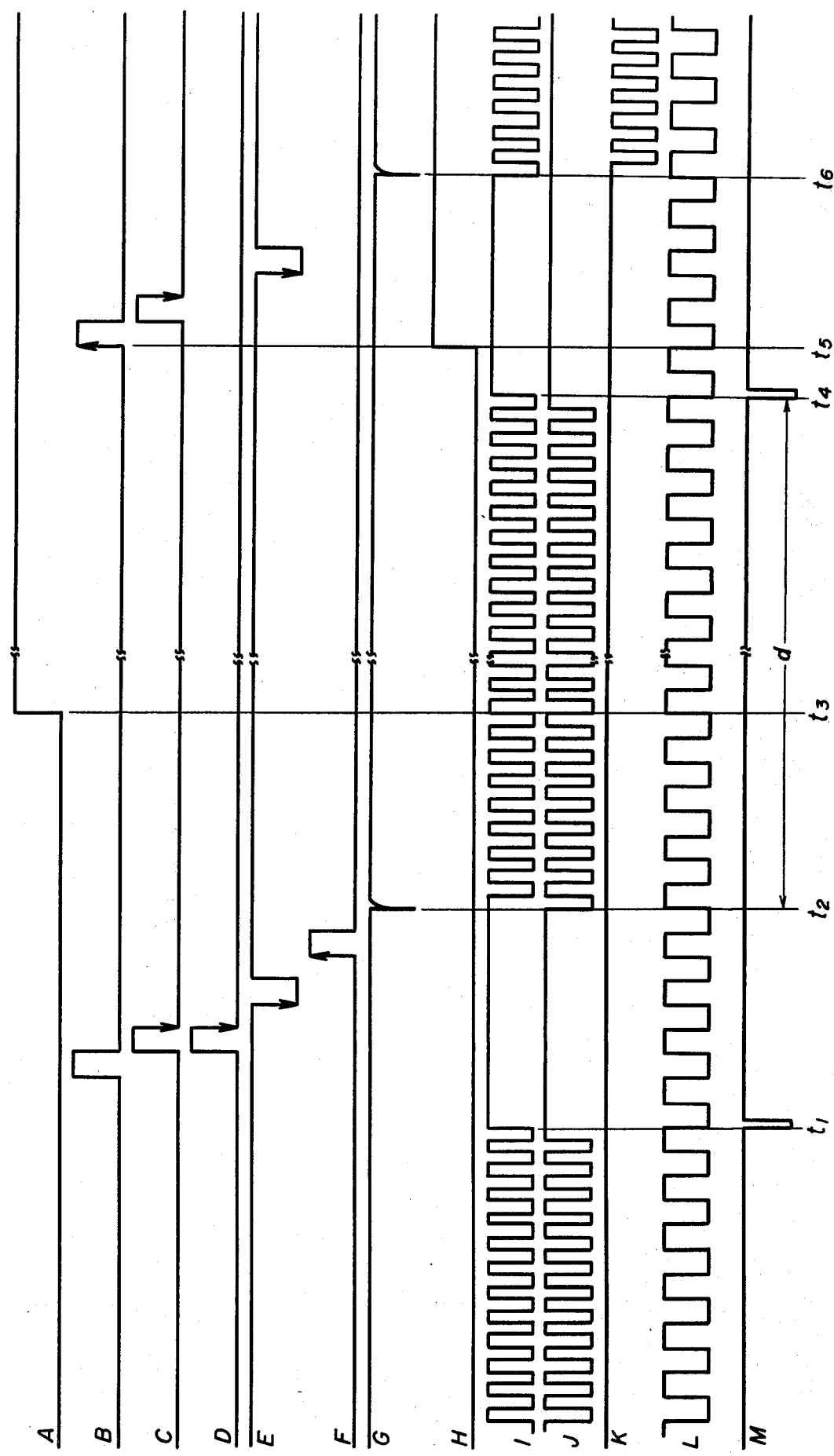
FIG. 2 depicts wave forms at various points in the block diagram of FIG. 1.

When the timer period produced by the timer 225 had ended, at $t_3$ in FIG. 2, the latch 220 switches states and its output becomes high. The apparatus 10 will not immediately be affected, but rather will be permitted to complete the cycle then in process. The set input of the latch 230 becoming high has no effect thereon until its reset input becomes low which in turn does not occur until an enable pulse appears on the "a" output of the stepping circuit 150. Pulses passing through the signal gate 90 during the period $t_2-t_4$ as shown in FIG. 2I are applied through the signal gate 160 as shown in FIG. 2J, even through the switch 75 has been placed in its "P" position and the 2 second period has lapsed. The counter system 170 continues to count up to $t_4$.

At the next negative transition of a clock pulse, at $t_5$, the stepping circuit 150 commences a new cycle and an enable pulse commencing at time $t_5$ is produced on the "a" output of the stepping circuit 150.

The latch 230 switches states and the Q and $\overline{Q}$ outputs reverse their logic levels causing the control gates 240 and 245 and the signal gate 160 to become disabled and the signal gate 165 to become enabled.

The pulse on the second output "b" is coupled to the control gate 240 but that has no effect since it is disabled. Note the absence of a pulse in FIG. 2D after $t_5$. Thus, the number on the preset input of the counter system 170 is not changed, but is maintained at the number equal to $F_uMN$ times the predetermined time interval. The enable pulse on the "b" output is inverted by the inverter 250 as shown in FIG. 2C and applied to the control input of the display latch system 190. A number previously counted by the counter system 170 is thus coupled through the system 190 to appear on the display 210. The number on the display 210 would represent the result of counting up pulses (FIG. 2J) during the time $t_2-t_4$ because the counter system 170 would have retained the number before time $t_5$. The enable pulse on the "c" output of the stepping circuit 150 loads the counter system 170 with the number which is continuously present on its preset input. The enable pulse on the "d" output of the stepping circuit 150 has no effect because it is applied to the disabled control gate 245. Note the absence of a pulse in FIG. 2F after $t_5$. Thus, the counter system 170 does not become cleared. The enable pulse on the "e" output resets the latch 140 to start a timer signal at time $t_6$.

A chain of pulses starting at $t_6$ as shown in FIG. 2I from the signal gate 90 are coupled through the signal gate 165 which is operative after $t_5$ as shown in FIG. 2K. These pulses are coupled to the down input of the counter system 170. After termination of the timer signal, another cycle of the stepping circuit 150 occurs. The output of the counter system 170 represents the number of pulses remaining in the counter system 170 after counting down from the number at the preset input derived during the up count. The next enable pulse on the "b" output of the stepping circuit 150 causes such remainder to be coupled through the display latch system 190 to appear on the display 210. The displayed number persists until the next cycle of the stepping circuit 150.

The number appearing on the display 210 in this example would be zero. The number at the preset input of the counter system 170 obtained during the up counting phase is precisely that counted during the down counting phase. The counter system 170 is counted up, for example, to 1,500 pulses and then counted back down 1,500 pulses to zero.

When the apparatus 10 is in the P mode, the decimal point 262 between the third and fourth digits of the display 210 is activated (XXX.XX). That decimal point is fed through an inverter 263 from the latch 220. Other formats would be acceptable such as "pounds×10."

When the bolt 11 is stressed or loaded, the load in pounds appears on the display 210. The Heyman system 15 changes the frequency as the bolt is loaded, always insuring that the same node is utilized. The decrease in the resonant frequency will be reflected as a decrease in the number of pulses from the signal gate 90 which in turn causes the number of pulses applied to the down input of the counter system 170 to decrease. The counter system 170 continues to count down from the unloaded frequency applied at the preset input so that remaining in the counter system is a number of pulses are representative of the load on the bolt 11. As the bolt 11 is tightened further, the display 210 continues to change at the rate of the predetermined time interval. In the example the display 210 is updated every 0.2 second.

The apparatus 10 gives extremely accurate digital information on the actual load in the bolt. The load appearing on the display is continuously updated so that the operator is able to obtain reasonably instantaneous values as he is tightening the bolt. The apparatus 10 is small and light weight so that it is portable. The apparatus 10 has no effect on the bolt 11 itself which is not the case with systems that require tightening of the bolt to its yield point. The accuracy is improved because the friction or torque-tension relationship is not a factor.

In the foregoing example, as depicted in FIG. 1, the bolt 11 is initially unloaded. When the bolt is thereafter loaded, the apparatus 10 quantitatively determines the load in the bolt.

There are situations when one would use the apparatus 10 as an inspection tool and determine whether a representative bolt already loaded has the correct load therein. This can be accomplished by reversing the clock inputs to the gates 160 and 165. In other words, couple the Q output of the latch 230 to the clock input of the signal gate 165 and couple the $\bar{Q}$ to the clock input of the signal gate 160. The frequency of resonance of the bolt 11 is first determined by placing the switch 75 in the "F" position. Then the factor M is calculated. When the switch 75 is thereafter placed in the "P" position, pulses representative of the frequency of resonance are coupled to the down input of the counter system 170. When the bolt 11 is thereafter unloaded, the counter system 170 will count up, past zero, so to speak. The display 10 will provide a number representative of the load that had been in the bolt 11.

Actually, the apparatus 10 supplies the difference in load between a first loaded condition of the bolt 11 and a second loaded condition. In the example explained and shown in FIG. 1, the first loaded condition really means an unloaded bolt and the second loaded condition means the load to which the bolt is tightened. In this case, the change in load corresponds to the actual load placed on the bolt. As an inspection tool, the first loaded condition corresponds to a bolt which is loaded, while the second loaded condition corresponds to an unloaded bolt. The information derived in this instance is the load originally in the bolt.

Although $F_u$ (or $F_p$ when the apparatus 10 is used as an inspection tool) can be determined in the above manner to calculate the factor M in certain instances it would be sufficient to approximate $F_u$ because it does not change significantly. For example, $F_u$ could be approximated at 5 mHz.

It is noteworthy that the apparatus 10 operates in so-called "real time". The information is continuously updated with negligible delay. This feature may be significant when the apparatus 10 is used to feed back to a device which controls the load on the bolt 11.

Figure 3:
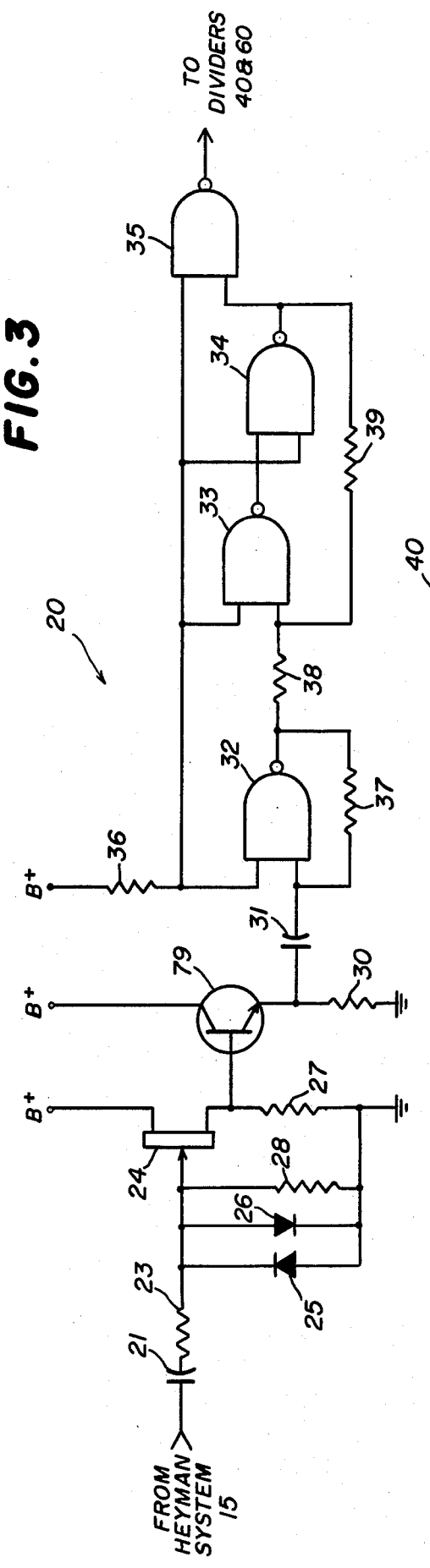

Turning now to FIG. 3, further details of the square wave generator 20 will be described. Generally, the generator 20 provides an interface between the Heyman system 15 and the balance of the apparatus 10 described herein. Input from the Heyman system is through a coupling capacitor 21 and a resistor 23 to a field effect transistor 24 which provides high input impedance. A pair of oppositely poled diodes 25 and 26 limit the amplitude of the signal applied to the transistor 24. The transistor 24 is connected in a common drain mode with a load resistor 27 between the source electrode and ground. The resistor 28 furnishes bias for the gate electrodes. The source electrode is coupled to the base of an NPN transistor 29 connected as an emitter follower, its load resistance 30 being coupled between the emitter and ground. The emitter is connected through a capacitor 31 to four inverting amplifiers 32, 33, 34 and 35 biased by resistors 36, 37, 38 and 39. The generator 20 squares the somewhat irregular sine wave from the Heyman system 15.

Figure 4:
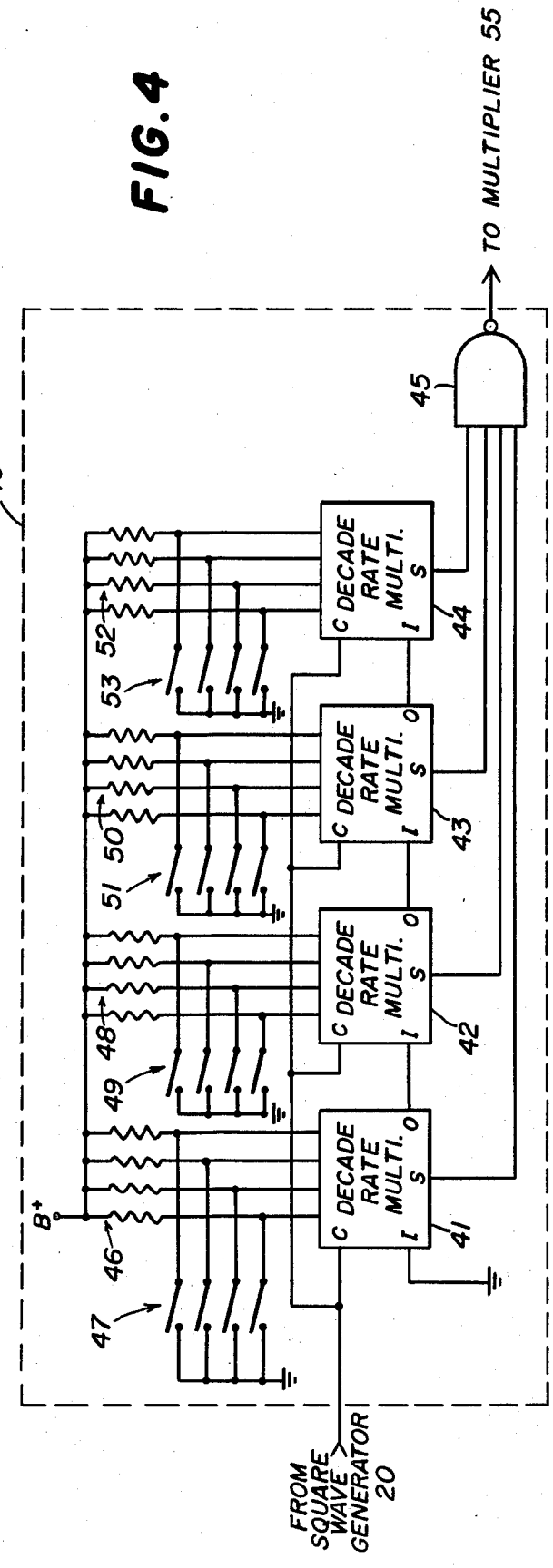

FIG. 4 depicts details of the multiplier 40, which includes a set of four cascaded synchronous decade rate multipliers 41, 42, 43 and 44. The clock inputs C of the multipliers 41–44 are connected together and to the output of the square wave generator 20. The enable output O of each multiplier is connected to the enable input I of the next multiplier. The signal outputs S of the multipliers 41–44 are respectively coupled to the four inputs of a NAND gate 45. The rate inputs of the multiplier 41 are coupled through bias resistors 46 to the B+ supply voltage and to a set of four switches ganged to provide a binary thumb wheel 47. Similarly, the rate inputs of the multiplier 42 are connected to bias resistors 48 and a thumb wheel 49, the multiplier 43 is connected to bias resistors 50 and a thumb wheel 51, and the multiplier 44 is connected to bias resistors 52 and a thumb wheel 53. In an actual operating embodiment, each of the multipliers 41–44 was a device made by Texas Instruments under its model No. SN74167. The thumb wheels 47, 49, 51 and 53 are accessible to the operator and each represents one digit of the multiplier factor M. Thus, if it is calculated that M is 0.3367 then the thumb wheel 47 will be set at 3, the thumb wheel 49 at 3, the thumb wheel 51 at 6 and the thumb wheel 53 at 7. The multiplier 40 serves to multiply the frequency of the signal from the square wave generator 20 by the inverse of the number programmed into the thumb wheel, 0.3367 in this example.

Although in the particular embodiment described, M is calculated by the operator. It should be understood that a suitably programmed microprocessor could be used instead. The operator would input data on the geometry and composition of the bolt set forth in the formula for calculating M. In an actual embodiment, the N multiplier 55 and the R multiplier 60 were so-called decade counters made by Texas Instruments under its model No. SN7490A.

Figure 5:
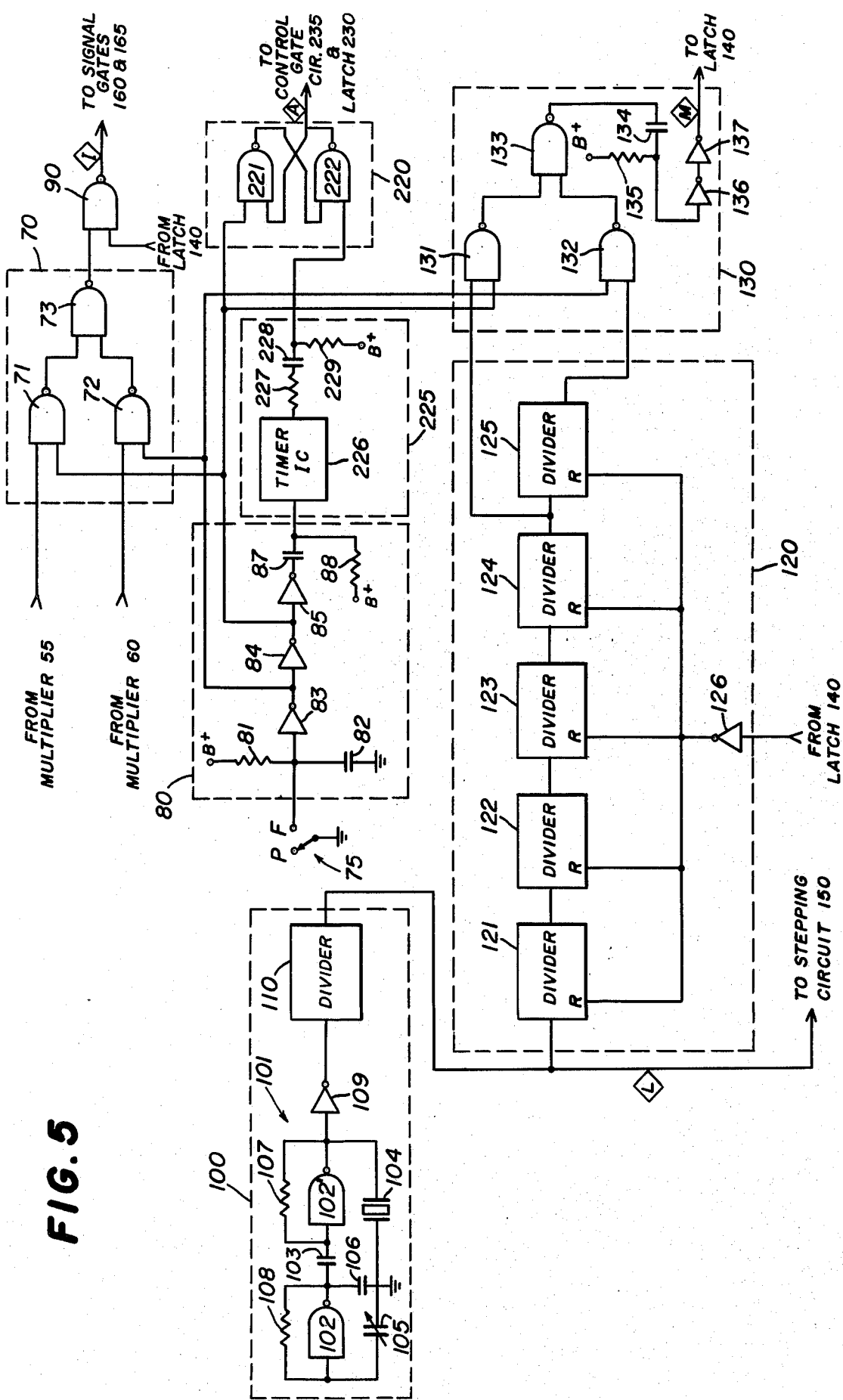

Turning now to FIG. 5, details of the additional ones of the circuits in the blocks of FIG. 1 will be described. The signal gate circuit 70 has two NAND gates 71 and 72, the signal inputs to which are respectively coupled to the multiplier 55 and the multiplier 60. Thus, on the signal input to the gate 71 is a signal with a frequency FMN and on the signal input of the NAND gate 72 is a signal with a frequency FR. The control input of the NAND gates 71 and 72 is derived from the control circuit 80. When the control input of a NAND gate is high, it is operative, that is, signals on its signal input are gated through. On the other hand, when the control input is low, the output of a NAND gate is high and the signal input has no effect. In the load mode, the control input of the NAND gate 71 is high as previously described in order to coupled through a signal with the frequency FMN from the multiplier 55, and the control input of the gate 72 is low to preclude getting through the signal with frequency FR. On the other hand, in the frequency mode of the apparatus 10, the control input of the gate 71 becomes low and the control input of the gate 72 becomes high to couple through the signal with frequency FR.

The outputs of the NAND gates 71 and 72 are respectively coupled to the inputs of a further NAND gate 73. As just described, the output of the one of the NAND gates 71 and 72 which is not operative will be high causing the NAND gate 73 to be operative to gate through the signal from the other one of the NAND gates.

The single pole, double throw switch 75 is coupled to the junction of a resistor 81 and a capacitor 82 connected to series between the B+ supply voltage and ground. The P terminal of the switch 75 is also connected to a series of inverter amplifiers 83, 84 and 85. Thus, in the P position of the switch 75, the input to the amplifier 83 is high whereby the output thereof is low and the output of the amplifier 84 is high. In the F position of the switch 75, the input of the amplifier 83 is grounded so that the output is high and the output of the amplifier 84 is low. The voltages from the amplifiers 83 and 84 are applied to the control inputs of the signal gate circuits 70 and 130 to control their operation.

The output of the amplifier 85 is coupled through a differentiating circuit defined by a series capacitor 87 and a shunt resistor 88 connected to the B+ supply voltage. When the switch 75 is in the F position, the output of the amplifier 85 is high. When the switch 75 is moved to the P position, the negative transition on the output of the amplifier 85 produces a negative pulse.

The output of the amplifier 84 is coupled to the set input of a latch 220 having a pair of NAND gates 221 and 222 cross connected as shown. In the P position of the switch 75, the input to the gate 221 is high as is the input of the gate 222. The output of the latch 20, appearing on the output of the NAND gate 222, is therefor low. Moving the switch 75 to the F position sets the latch 220 by causing the input to the gate 221 to become low. However, the output of the gate 222 is not affected and remains low.

The spike from the capacitor 87 in the control circuit 80 is applied to the timer 225 which includes a timer integrated circuit 226 the output of which is coupled to a resistor 227 and a capacitor 228, a resistor 229 being coupled to the supply voltage. The spike on the input of the timer integrated circuit 226 causes operation of same. Other components (not shown) connected thereto determine when its output becomes low. The negative transition is differentiated by the components 227-229, and applied to the reset input of the latch 220, namely the input to the NAND gate 222, whereby its output becomes high. See FIG. 2A, at $t_3$.

In an operating embodiment of the invention, the output of the timer 225 occurs two seconds after the spike is applied to its input.

The clock 100 includes an oscillator 101 defined by a pair of NAND gates 102 and 102' connected as inverters with a coupling capacitor 103 between them. A crystal 104 is coupled in series with a trimmer capacitor 105 as feedback. The capacitor 105 together with a crystal 104 determines the frequency of oscillation. The capacitor 106 and resistors 107 and 108 bias the gates 102 and 102' into oscillation. In an operating embodiment, the oscillator 101 produced a signal at a frequency of 1 mHz which was inverted by a buffer amplifier 109 and applied to a divider 110 which divided the frequency by a factor of 10.

The 100 kHz signal is applied to a divider chain 120 having divider IC's 121-125 which dividers are not free running but rather operate only when a reset voltage is removed to the reset inputs R. Each divider divides the frequency by 10 and multiplies the period by 10 so that the output of the divider 124 appears 0.1 second after a reset voltage is removed to the dividers 121-125. The divider 125 multiplies the period by two so that an output from the divider 125 appears about 0.2 second after the dividers 121-125 are released from reset. The voltage from the latch 140 is inverted by an inverter 126 and coupled to the reset inputs of the dividers 121-125.

The signal gate circuit 130 has two NAND gates 131 and 132, the signal inputs to which are respectively coupled to the output of the divider 125 and the output of the divider 125. Thus, on the signal input to the gate 131 is a signal that lasts for 0.1 second and on the signal input of the NAND gate 132 is a signal that lasts for 0.2 second. The control inputs of the NAND gates 131 and 132 are derived from the control circuit 80. When the control input on a NAND gate is high, it is operative, that is, signals on its signal input are gated through. On the other hand, when the control input is low, the output of a NAND gate is high and the signal input has no effect. In the frequency mode, the control input to the NAND gate 131 is high as previously described in order to couple through the 0.1 second time signal from the divider 124, and the control input of the gate 132 is low to preclude gating through the 0.2 second time signal. On the other hand, in the load mode of the apparatus 10, the control input of the gate 131 becomes low and the control input of the gate 132 becomes high to couple through the 0.2 second interval.

The outputs of the NAND gates 131 and 132 are respectively coupled to the inputs of a further NAND gate 133. As just described, the output of the one of the NAND gates 131 and 132 which is not operative will be high causing the NAND gate 133 to be operative to gate through the timer signal from the other one of the NAND gates. The output of the NAND gate 133 is coupled through a differentiating circuit comprising a series capacitor 134 and a shunt resistor 135 to the B+ supply voltage. The differentiating circuit responds to the termination of the 0.1 or 0.2 second timer signal, as the case may be, to produce a negative going spike which is squared by buffer amplifiers 136 and 137 as depicted in FIG. 2M.

Figure 6:
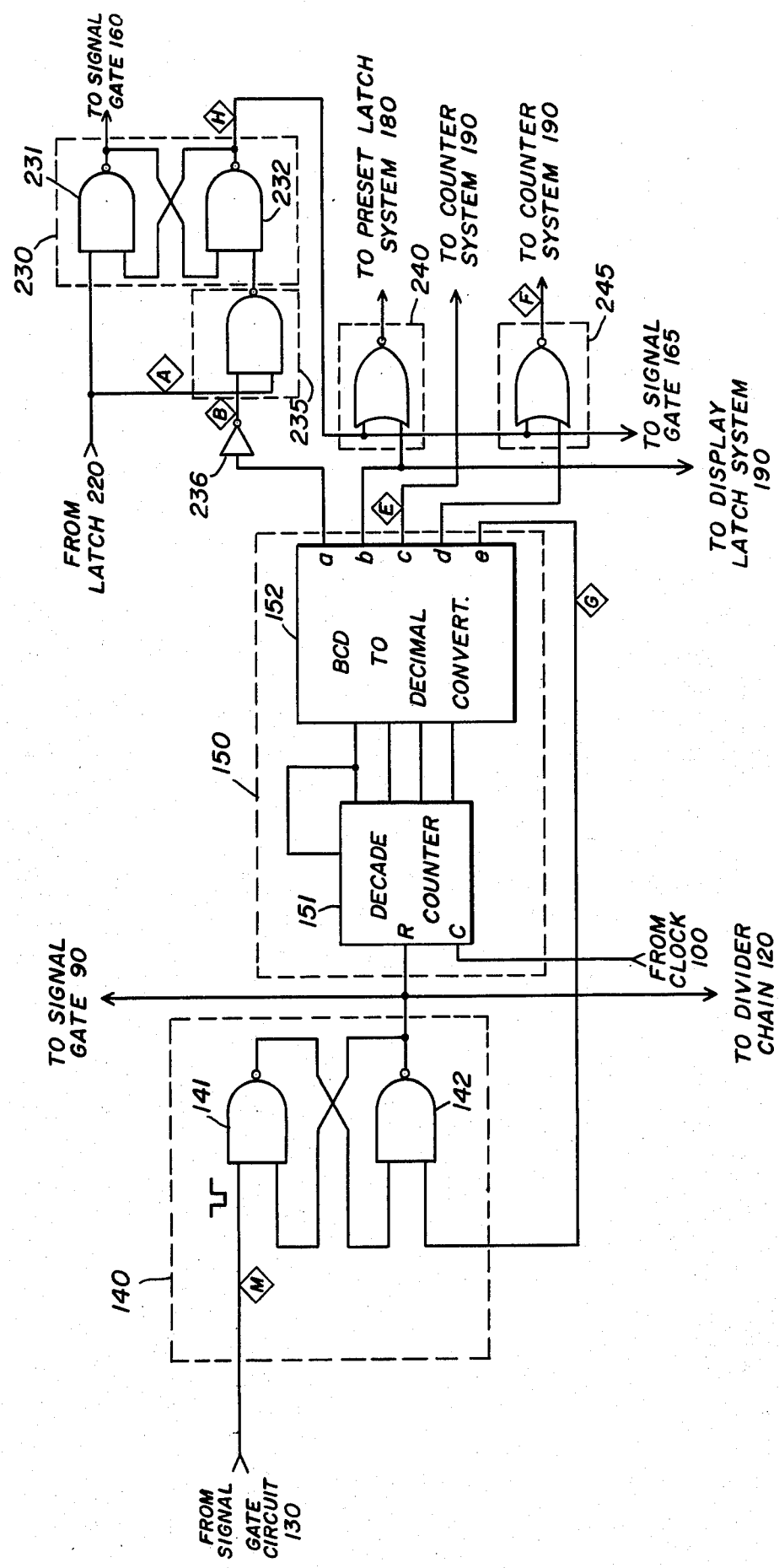

Further details of the latches 140 and 230, and the stepping circuit 150 are depicted in FIG. 6. The latch 140 includes a pair of cross connected NAND gates 141 and 142. The output of the NAND gate 141 is connected to one input of the NAND gate 142, the other input of which is coupled to one input of the NAND gate 141. The remaining input of the NAND gate 141 constitutes the set input of the latch 140 and the other input of the NAND gate 142 constitutes its reset input. Normally, both inputs are high and the output of the latch 140 appearing on the output of the NAND gate 142 is normally low. After the stepping circuit 150 has gone through a cycle, a pulse appears on its "e" output as previously explained, causing the second input of the NAND gate 142 to become low. The output of the NAND gate 142 becomes high thereby commencing the timer signal. As soon as the latch 140 has been reset in this manner, the pulse on the input of the gate 142 terminates and its input again becomes high, which has no effect on the output of the NAND gate 142 and its output remains high. After a predetermined time, a pulse from the signal gate circuit 130 is applied to the second input of the gate 141 causing its input to become low causing the output of the NAND gate 142 to again become low thereby terminating the timer signal. On termination of the pulse from the signal gate circuit 130 the input of the NAND gate 141 again becomes high which has no effect on the output of the NAND gate 142.

The stepping circuit 150 includes a decade counter 151 and a BCD to decimal converter 152. The decade counter has a reset input R coupled to the latch 140, a clock input C coupled to the clock 100 and a binary output which is coupled to the converter 152. The converter 152 in turn is shown to have five outputs "a" to "e". Actually, in an operative embodiment, the converter had five additional outputs which were not utilized. In that embodiment, the "a" output was the first output and the "b" output was the second output but the "c" output was the fourth output, the "d" output was the sixth output and the "e" output was the eighth output. This can be seen in the time relationship of the pulses in FIGS. 2B-2G. In such operative embodiment, the decade counter 151 was a device made by Texas Instruments under its model No. SN7490A. The BCD to decimal converter was also made by Texas Instruments under its model No. SN7442A. During the predetermined time intervals, the output of the latch 140 is high and therefore the decade counter 151 is not operative. Between such intervals, the reset input is low and the counter 151 counts pulses from the clock 100 and produces a binary output at the rate of such pulses. The BCD to decimal converter has its outputs become high in succession at the clock rate. Assuming a 100 kHz rate, each output is high for about ten $\mu s$ and a full cycle of the stepping circuit takes about 100 $\mu s$.

The latch 230 includes a pair of NAND gates 231 and 232. The output of the NAND gate 231 is connected to one input of the NAND gate 232, the output of which is connected to one input of a NAND gate 231. The second input of the NAND gate 231 constitutes the set input and its output constitutes a $\overline{Q}$ output. The second input of the gate 232 constitutes the reset input and its output is the Q output. The control gate 235 is simply a NAND gate having its output connected to the second input of the NAND gate 232. One input of the gate 235 is coupled to the latch 220 and the remaining input is coupled to the inverter 236 to the output of the converter 152.

When the switch 75 is in the frequency position, the output of the latch 220 is low whereby the output of the gate 235 is high. Accordingly, the output of the gate 231 is high and the output of the gate 232 is low. When the manual switch 75 is placed in the load or "P" position, the output of the latch 220 will become high about two seconds later in the example given above, causing the second input of the gate 231 to become high. One input of the gate 235 also becomes high which has no immediate effect thereon. Accordingly, the latch 230 is not affected by placing the switch 75 in its "P" position or even two seconds thereafter. The next time the stepping circuit 150 goes through a cycle, the "a" output will become low and the second input to the gate 235 will thus become high and its output low. The latch 230 switches conditions such that the output of the gate 232 becomes high and the output of the gate 231 becomes low.

When the apparatus 10 is in its frequency position, the output of the NAND gate 232 is low meaning that the NOR gates 240 and 245 are operative to gate through signals applied to their signal inputs. Thus, they will gate through the pulses that occur on the "b" and "d" outputs of the converter 152. The gates 240 and 245 remain in their operative conditions for two seconds after placing the switch 75 in its "P" condition. Thereafter, the control inputs of gates 240 and 245 become high and they become inoperative because their outputs are low irrespective of what is applied to their signal inputs.

Additional details of the apparatus 10 are depicted in FIG. 7. The signal gates 160 and 165 are NAND gates having their control inputs respectively coupled to the Q and $\overline{Q}$ outputs of the latch 230. Their signal inputs are coupled together and to the output of the signal gate 90. Prior to $t_5$, the control input of the gate 160 is high so that it is operative to gate through signals from the signal gate 90 to the up input of the counter system 170. The control input of the gate 165 is low so that it is inoperative before $t_5$. At $t_5$, the latch 230 switches conditions and the gate 160 becomes inoperative and the control input of the gate 165 becomes high so that pulses from the signal gate 90 are gated through to the down input of the counter system 170.

The counter system 170 in this particular embodiment includes five individual counters 171-175 each having an up input U, down input D, a clear input C, a load input L, a preset input P and two sets of outputs $0_1$ and $0_2$. The up input of the first counter 171 is connected to the gate 160 and its down input is connected to the gate 165. The output set $0_2$ of the counter 171 is connected to the up and down inputs of the counter 172, etc. The clear inputs are connected together and to the control gate 245, while the L inputs are connected together and to the stepping circuit 150. Each of the counters takes care of one of the five decades of counting corresponding to the digit being displayed. Thus, when the counter system 170 is cleared or loaded as previously explained, all of the counters 171-175 are simultaneously cleared or loaded. In an operative embodiment, each of the counters was made by Texas Instruments under model No. SN74192.

The preset latch 180 includes five preset latches 181-185. Each such preset latch has signal inputs S, a control input C and outputs Q. The four inputs S are respectively coupled to the four outputs $0_1$ of the counter 171. When a control signal is applied to the control input C, whatever information is present on the four inputs S are transferred respectively to the four outputs Q which are in turn respectively coupled to the preset inputs P of the counter 171. These are binary numbers so that when the preset latch 181 is switched, there will appear at the P input a number from which the counter 171 can count down in the presence of a signal applied to its down input. The signal on the Q output will remain until the next time a control signal is applied to the C input, whereupon whatever is present at the S inputs at that instant will be transferred to the Q outputs. The control inputs of the preset latches 181–185 are connected together and to the control gate 240 so that a control signal switches the conditions of all simultaneously. The preset latches 182–185 are associated respectively with the counters 172–175 in the same manner. In an operative embodiment, each preset latch was made by Texas Instruments under its model No. SN7475.

The display latch system 190 also includes five display latches 191–195. Each such display latch has signal inputs S, a control input C and outputs Q. The four inputs S are respectively coupled to the four outputs $O_1$ of the counter 171. When a control signal is applied to the control input C, whatever information is present on the four inputs S are transferred respectively to the four outputs Q. The binary signal on the Q outputs will remain until the next time a control signal is applied to the C input, whereupon whatever is present at the S inputs at that instant will be transferred to the Q outputs. The control inputs of the display latches 191–195 are connected together and to the inverter 250 so that a control signal switches the conditions of all simultaneously. The display latches 192–195 are associated respectively with the counters 172–175 in the same manner. In an operative embodiment, each display latch was made by Texas Instruments under its model No. SN7475.

The decoder system 200 includes five decoders 201–205 each converting BCD information on its input to seven segment information on its output. The binary information on the Q output of the display latch 191 is applied to the decoder 201 which converts that information into seven segment information. Similarly, each of the decoders 202–205 are respectively associated with the display latches 192–195. In an operative embodiment, each of the decoders 201–205 was made by Texas Instruments under its model No. SN 7447A.

The display system 210 includes five display units 211–215 each providing a seven segment digit illuminated in accordance with the information respectively supplied by the decoders to 201–205.

What has been described therefore is an improved apparatus for determining the load in a bolt. While example frequencies and times have been given, it is understood that other frequencies and times can be used as well. Also, while models of integrated circuits have been identified for use in the various circuits, other circuits are available which will also function. Finally, while there has been described what is at present considered to be the preferred embodiment of the invention, it is understood that various changes can be made therein yet come within the spirit and scope of the claims.

We claim:

1. Bolt load determining apparatus comprising means for providing a first pulsating signal at a first frequency being a selected harmonic of the resonant frequency of the bolt in a first loaded condition thereof and for thereafter providing a second pulsating signal at a second frequency being the same harmonic of the resonant frequency of the bolt in a second loaded condition thereof, means for multiplying the first frequency by a factor M dependent on the first frequency and the geometry and composition of the bolt and thereafter multiplying the second frequency by the factor M, counter means having an up input to receive pulses to be counted up from zero and a down input to receive pulses to be counted down from the number counted at said up input, means for coupling the first pulsating signal to one of said inputs for a predetermined duration and for thereafter coupling the second pulsating signal to the other of said inputs for the predetermined duration, and means for indicating the number of pulses remaining in said counter means which number is representative of the difference in load on the bolt between the first and second loaded conditions.

2. The bolt load determining apparatus of claim 1, wherein the load on the bolt in the first loaded condition thereof is zero, the first pulsating signal being coupled to said up input and the second pulsating signal being coupled to said down input.

3. The bolt load determining apparatus of claim 1, wherein the load on the bolt in the second loaded condition thereof is zero, the first pulsating signal being coupled to said down input and the second pulsating signal being coupled to said up input.

4. The bolt load determining apparatus of claim 1, wherein the factor M is less than one.

5. The bolt load determining apparatus of claim 1, wherein said multiplying means includes means for multiplying the first frequency by an additional factor.

6. Bolt load determining apparatus of claim 1, wherein said predetermined duration is on the order of about 0.2 second.

7. The bolt load determining apparatus of claim 1, wherein said multiplying means includes means for multiplying the first frequency by an additional factor of 0.5, said predetermined duration being 0.2 second.

8. The bolt load determining apparatus of claim 1, wherein the factor $$M = \left[ \frac{LE}{F_u K} \left( \frac{A_{t1}}{L_{t1}} + \frac{A_{t2}}{L_{t2}} + \frac{A_u}{L_u} \right) \right],$$

in which L is the length of the bolt, E is Young's modulus, $F_u$ is the first frequency, K is a factor dependent on the composition of the bolt, $A_u$ and $L_u$ are respectively the cross-sectional area and length of the unthreaded portion of the bolt, $A_{t1}$ and $L_{t1}$ are respectively the cross-sectional area and length of that part of the threaded portion of the bolt between the head and the nut, and $A_{t2}$ and $L_{t2}$ are respectively the cross-sectional area and effective length of that part of the threaded portion of the bolt within the nut.

9. Bolt load determining apparatus of claim 1, and further comprising means for squaring the pulsating signals.

10. A method for determining the load in a bolt comprising the steps of providing a bolt in a first loaded condition, providing a first pulsating signal at a first frequency being a selected harmonic of the resonant frequency of the bolt in the first loaded condition, multiplying the first frequency by a factor M dependent on the first frequency and geometry and composition of the bolt, counting the number of pulses for the first pulsating signal for a predetermined duration, storing such number, changing the loading on the bolt to a second loaded condition, providing a second pulsating signal at a second frequency being the same selected harmonic of the resonant frequency of the bolt in its second loaded condition, multiplying the second frequency by the factor M, counting away from the stored number the number of pulses of the second pulsating signal for the same predetermined duration, and indicating the number of pulses remaining after counting away from the stored number.

11. The method of claim 10, wherein the load in the bolt in the first loaded condition thereof is zero.

12. The method of claim 10, wherein the load in the bolt in the second loaded condition thereof is zero.

13. Bolt load determining apparatus comprising means for providing a first pulsating signal at a first frequency being a selected harmonic of the resonant frequency of the bolt in a first loaded condition thereof and for thereafter providing a second pulsating signal at a second frequency being the same harmonic of the resonant frequency of the bolt in a second loaded condition thereof, means for multiplying the first frequency by a factor M dependent on the first frequency and the geometry and composition of the bolt and thereafter multiplying the second frequency by the factor M, first and second and third signal gates each having a signal input and a control input and an output, the signal input of said first signal gate being coupled to said multiplying means, timer means for providing a timer signal having a predetermined duration, said timer means being coupled to the control input of said first signal gate for enablement thereof for the predetermined duration, thereby to gate through the first pulsating signal and thereafter the second pulsating signal, the signal inputs of said second and third signal gates being coupled to the output of said first signal gate, counter means having an up input to receive pulses to be counted up from zero and a down input to receive pulses to be counted down from the number counted at the up input, the output of said second signal gate being coupled to said up input and the output of said third signal gate being coupled to said down input, means coupled to the control inputs of said second and third signal gates to enable said second signal gate generally when said bolt is in one of the loaded conditions and to enable said third signal gate generally when said bolt is in the other one of the loaded conditions, and means for indicating the number of pulses remaining in said counter means which number is representative of the difference in load on the bolt between the first and second loaded conditions.

14. Bolt load determining apparatus comprising means for providing a first pulsating signal at a first frequency being a selected harmonic of the resonant frequency of the bolt in a first loaded condition thereof and for thereafter providing a second pulsating signal at a second frequency being the same harmonic of the resonant frequency of the bolt in a second loaded condition thereof, means for multiplying the first frequency by a factor M dependent on the first frequency and the geometry and composition of the bolt and thereafter multiplying the second frequency by the factor M, first and second and third signal gates each having a signal input and a control input and an output, the signal input of said first signal gate being coupled to said dividing means, timer means for providing a timer signal having a predetermined duration, said timer means being coupled to the control input of said first signal gate for enablement thereof for the predetermined duration, thereby to couple to the output of said first signal gate the first pulsating signal and thereafter the second pulsating signal, the signal inputs of said second and third signal gates being coupled to the output of said first signal gate, counter means having an up input to receive pulses to be counted up from zero and a down input to receive pulses to be counted down from the number counted at the up input, the output of said second signal gate being coupled to said up input and the output of said third signal gate being coupled to said down input, latch means coupled to the control inputs of said second and third signal gates and having a first condition to enable said second signal gate and a second condition to enable said third signal gate, manual switch means for placing said latch means in the first condition thereof when the bolt is in one of the loaded conditions and for placing said latch means in the second condition thereof prior to placing the bolt in the other loaded condition thereof and means for indicating the number of pulses remaining in said counter means which number is representative of the difference in load on the bolt between the first and second loaded conditions.

15. The bolt load determining apparatus of claim 14, and further comprising means for maintaining said latch means in the first condition thereof for a predetermined time following operation of said manual switch means to ensure that said counter means first receives pulses at said up input.

16. Bolt load determining apparatus comprising means for providing a first pulsating signal at a first frequency $F_u$ being a selected harmonic of the resonant frequency of the bolt in its unloaded condition and for thereafter providing a second pulsating signal at a second frequency $F_p$ being the same harmonic of the resonant frequency of the bolt in its loaded condition, multiplier means for multiplying the first frequency by a factor M dependent on the first frequency and on the geometry and composition of the bolt and thereafter multiplying the second frequency by the factor M, circuit means for providing a signal having a frequency proportional to the first frequency and thereafter providing a signal having a frequency proportional to the second frequency, a signal gate having signal input means coupled to said multiplier means and to said circuit means and having an output and control input means, manual switch means coupled to said control input means and having a frequency position and a load position, said signal gate being operative when said manual switch means is in the frequency position to couple through signals from said circuit means and being operative when said manual switch means is in the load position to couple through signals with a frequency multiplied by the factor M, counter means having an up input to receive pulses to be counted up from zero and a down input to receive pulses to be counted down from the number counted at said up input, means for coupling the pulsating signal from said circuit means to said up input for a first predetermined duration and for coupling the pulsating signal having a frequency $MF_u$ to said up input for a second predetermined duration and for coupling the pulsating signal having the frequency $MF_p$ to said down input for the second predetermined duration, and means for indicating the number of pulses of the pulsating signal from said circuit means counted by said counter means and for indicating the number of pulses remaining in said counter means after counting the number of pulses having the frequency $MF_p$.

17. The bolt load determining apparatus of claim 16, wherein the frequency of the signal provided by said circuit means is not equal to the first or second frequency.

18. The bolt load determining apparatus of claim 16, wherein said first predetermined duration is different from said second predetermined duration.

19. The bolt load determining apparatus of claim 16, wherein said multiplier means includes means for multiplying the first frequency by an additional factor.

20. The bolt load determining apparatus of claim 19, wherein said additional factor is 0.5 and said second predetermined duration is 0.2 second.

21. Bolt load determining apparatus of claim 16, wherein said circuit means multiplies the first and second frequencies by 0.1 and said first predetermined duration is 0.1 second.

22. Bolt load determining apparatus comprising means for providing a first pulsating signal at a first frequency $F_u$ being a selected harmonic of the resonant frequency of the bolt in its unloaded condition and for thereafter providing a second pulsating signal at a second frequency $F_p$ being the same harmonic of the resonant frequency of the bolt in its loaded condition, multiplier means for multiplying the first frequency by a factor M dependent on the first frequency and on the geometry and composition of the bolt and thereafter multiplying the second frequency by the factor M, first circuit means for providing a signal having a frequency proportional to the first frequency and thereafter providing a signal having a frequency proportional to the second frequency, a first signal gate having signal input means coupled to said multiplier means and said first circuit means and having an output and control input means, manual switch means coupled to said control input means and having a frequency position and a load position, said first signal gate being operative when said manual switch means is in the frequency position to couple through signals from said circuit means, and being operative when said manual switch means is in the load position to couple through signals with a frequency multiplied by the factor M, second, third and fourth signal gates each having a signal input and a control input and an output, the signal input of said second signal gate being coupled to the output of said first signal gate, timer means coupled to said manual switch means and being operative to provide a timer signal having a first predetermined duration when said manual switch means is in the frequency position and to provide a timer signal having a second predetermined duration when said manual switch means is in the load position, said timer means being coupled to the control input of said second signal gate for enablement thereof for the duration of the timer signal, thereby to gate through the first pulsating signal and thereafter the second pulsating signal, the signal inputs of said third and fourth signal gates being coupled to the output of said second signal gate, counter means having an up input to receive pulses to be counted up from zero and a down input to receive pulses to be counted down from the number counted at the up input, the output of said third signal gate being coupled to said up input and the output of said fourth signal gate being coupled to said down input, second circuit means coupled between said manual switch means and the control inputs of said third and fourth signal gates to enable said third signal gate when said manual switch means is in the frequency position and to continue to enable said third signal gate for a predetermined time after said manual switch means is moved to the load position and thereafter to enable said fourth signal gate, and means for indicating the number of pulses of the pulsating signal counted by said counter means when said manual switch means is in the frequency position and for indicating the number of pulses remaining in said counter means after said manual switch means is placed in the load position.

23. Bolt load determining apparatus comprising means for providing a first pulsating signal at a first frequency being a selected harmonic of the resonant frequency of the bolt in a first loaded condition thereof and for thereafter providing a second pulsating signal at a second frequency being the same harmonic of the resonant frequency of the bolt in a second loaded condition thereof, means for multiplying the first frequency by a factor M dependent on the first frequency and the geometry and composition of the bolt and thereafter multiplying the second frequency by the factor M, first and second and third signal gates each having a signal input and a control input and an output, the signal input of said first signal gate being coupled to said multiplying means, latch means for providing a timer signal having a predetermined duration and having a reset input and an output, a stepping circuit coupled to the output of said latch means and having a plurality of outputs on which enabling pulses successively appear starting with the termination of the timer signal, one of the outputs of said stepping circuit being coupled to the reset input of said latch means, said latch means being responsive to the enabling pulse on the last output of said stepping circuit to commence the timer signal, circuit means coupled to the output of said latch means for producing a termination pulse a time after commencement of the timer signal equal to the predetermined duration, said latch means being responsive to the termination pulse to terminate the timer signal, said latch means being coupled to the control input of said first signal gate for enablement thereof for the predetermined duration, thereby to gate through the first pulsating signal and thereafter the second pulsating signal, the signal inputs of said second and third signal gates being coupled to the output of said first signal gate, counter means having an up input to receive pulses to be counted up from zero and a down input to receive pulses to be counted down from the number counted at the up input, the output of said second signal gate being coupled to said up input and the output of said third signal gate being coupled to said down input, means coupled to the control inputs of said second and third signal gates to enable said second signal gate generally when said bolt is in the first loaded condition thereof and to enable said third signal gate generally when said bolt is in the second loaded condition thereof and means for indicating the number of pulses remaining in said counter means which number is representative of the difference in load on the bolt between the first and second loaded conditions.

24. The bolt load determining apparatus of claim 23, and further comprising a clock for producing a pulsating signal for said circuit means and for said stepping circuit.

25. The bolt load determining apparatus of claim 23, wherein the last output of said stepping circuit is coupled to the reset input of said latch means.

26. The bolt load determining apparatus of claim 23, wherein said circuit means includes a clock for producing a pulsating signal, and a divider chain coupled to said clock for dividing the frequency of the pulses to a lower value, said circuit means having a reset input coupled to the output of said latch means.

27. The bolt load determining apparatus of claim 23, wherein said third output of said stepping circuit is coupled to the load input of said counter means, said counter means being responsive to an enabling signal on said load output to load into said counter means the number on said preset input.

28. Bolt load determining apparatus comprising means for providing a first pulsating signal at a first frequency being a selected harmonic of the resonant frequency of the bolt in a first loaded condition thereof and for thereafter providing a second pulsating signal at a second frequency being the same harmonic of the resonant frequency of the bolt in a second loaded condition thereof, means for multiplying the first frequency by a factor M dependent on the first frequency and the geometry and composition of the bolt and thereafter multiplying the second frequency by the factor M, first and second and third signal gates each having a signal input and a control input and an output, the signal input of said first signal gate being coupled to said dividing means, first latch means for providing a timer signal having a predetermined duration and having a reset input and an output, a stepping circuit coupled to the output of said first latch means and having a plurality of outputs on which enabling pulses successively appear starting with the termination of the timer signal, one of the outputs of said stepping circuit being coupled to the reset input of said first latch means, said first latch means being responsive to the enabling pulse on the last output of said stepping circuit to commence the timer signal, circuit means coupled to the output of said first latch means for producing a termination pulse a time after commencement of the timer signal equal to the predetermined duration, said latch means being responsive to the termination pulse to terminate the timer signal, said first latch means being coupled to the control input of said first signal gate for enablement thereof for the predetermined duration, thereby to couple to the output of said first signal gate the first pulsating signal and thereafter the second pulsating signal, the signal inputs of said second and third signal gates being coupled to the output of said first signal gate, counter means having an up input to receive pulses to be counted up from zero and a down input to receive pulses to be counted down from the number counted at the up input, the output of said second signal gate being coupled to said up input and the output of said third signal gate being coupled to said down input, second latch means coupled to the control inputs of said second and third signal gates and having a first condition to enable said second signal gate and a second condition to enable said third signal gate, manual switch means for placing said second latch means in the first condition thereof when the bolt is in its first loaded condition and for placing said latch means in the second condition thereof prior to placing the bolt in its second loaded condition, and means for indicating the number of pulses remaining in said counter means which number is representative of the difference in load on the bolt between the first and second loaded conditions.

29. The bolt load determining apparatus of claim 28, wherein said counter means includes means for presetting to the number of pulses of the pulsating signal counted in the frequency position of said manual switch means, and further comprising a first control gate having a control input coupled to said latch means and being operable when said latch means is in the first condition, said first control gate having an input coupled to an intermediate output of said stepping circuit and having an output coupled to said preset latch means, said first control gate being operative in the presence of an enabling signal on its associated output to reset said counter means, a second control gate having its signal input coupled to a subsequent output of said stepping circuit and being operative in the presence of an enabling signal thereon to clear said counter means.

30. Bolt load determining apparatus for use with means that provides a first pulsating signal at a first frequency being a selected harmonic of the resonant frequency of the bolt in a first loaded condition thereof and that thereafter provides a second pulsating signal at a second frequency being the same harmonic of the resonant frequency of the bolt in a second loaded condition thereof, the combination comprising means for multiplying the first frequency by a factor M dependent on the first frequency and the geometry and composition of the bolt and thereafter multiplying the second frequency by the factor M, counter means having an up input to receive pulses to be counted up from zero and a down input to receive pulses to be counted down from the number counted at said up input, means for coupling the first pulsating signal to one of said inputs for a predetermined duration and for thereafter coupling the second pulsating signal to the other of said inputs for the predetermined duration, and means for indicating the number of pulses remaining in said counter means which number is representative of the difference in load on the bolt between the first and second loaded conditions.

* * * * *